US010952409B2

(12) United States Patent
Komatsubara

(10) Patent No.: US 10,952,409 B2
(45) Date of Patent: Mar. 23, 2021

(54) ABSORBENT ARTICLE FOR PET ANIMALS

(71) Applicant: Unicharm Corporation, Shikokuchuo (JP)

(72) Inventor: Daisuke Komatsubara, Kanonji (JP)

(73) Assignee: UNICHARM CORPORATION, Ehime (JP)

( * ) Notice: Subject to any disclaimer, the term of this patent is extended or adjusted under 35 U.S.C. 154(b) by 556 days.

(21) Appl. No.: 15/571,263

(22) PCT Filed: May 21, 2015

(86) PCT No.: PCT/JP2015/064555
§ 371 (c)(1),
(2) Date: Nov. 2, 2017

(87) PCT Pub. No.: WO2016/181568
PCT Pub. Date: Nov. 17, 2016

(65) Prior Publication Data
US 2018/0271064 A1    Sep. 27, 2018

(30) Foreign Application Priority Data

May 12, 2015 (JP) .............................. JP2015-097238

(51) Int. Cl.
*A01K 23/00* (2006.01)
*A61F 13/49* (2006.01)
*A61F 13/15* (2006.01)

(52) U.S. Cl.
CPC ........ *A01K 23/00* (2013.01); *A61F 13/49015* (2013.01); *A61F 13/49058* (2013.01); *A61F 2013/15186* (2013.01)

(58) Field of Classification Search
CPC .......... A61F 13/49015; A61F 13/49058; A61F 13/493; A61F 2013/15186;
(Continued)

(56) References Cited

U.S. PATENT DOCUMENTS 5,954,015 A * 9/1999 Ohta ...................... A01K 23/00
119/850
7,195,618 B2 * 3/2007 Ikegami ................ A01K 23/00
604/345

(Continued)

FOREIGN PATENT DOCUMENTS

JP    2004-159591 A    6/2004
JP    2012-187095 A    10/2012
(Continued)

OTHER PUBLICATIONS

International Search Report in PCT/JP2015/064555, dated Jun. 23, 2015. 2pp.

*Primary Examiner* — Catharine L Anderson
(74) *Attorney, Agent, or Firm* — Hauptman Ham, LLP

(57) ABSTRACT

Disclosed is an absorbent article for pet animals. The article has a longitudinal direction, a transverse direction, a body-facing surface, a non-body-facing surface and first and second ends opposed to each other in the longitudinal direction. The article includes: a tail facing area facing a pet animal's tail; a first section to cover one side of a pet animal's rump, extending from the tail facing area to the first end; a second section to cover the other side of the pet animal's rump, extending from the tail facing area to the second end; and an absorbent core disposed between the first and second sections.

10 Claims, 9 Drawing Sheets

(58) Field of Classification Search
CPC .. A61F 2013/49063; A61F 2013/49066; A61F 2013/49098; A01K 23/00
USPC .................................................. 604/385.09
See application file for complete search history.

(56) References Cited

U.S. PATENT DOCUMENTS

| | | | |
|---|---|---|---|
| 2006/0149203 A1* | 7/2006 | Draper | A01K 23/00 604/385.09 |
| 2014/0090608 A1* | 4/2014 | Komatsubara | A01K 23/00 119/869 |
| 2015/0045762 A1 | 2/2015 | Komatsubara | |

FOREIGN PATENT DOCUMENTS

| | | |
|---|---|---|
| JP | 2013-46587 A | 3/2013 |
| JP | 5602973 B1 | 10/2014 |
| JP | 2015-29467 A | 2/2015 |

* cited by examiner

ABSORBENT ARTICLE FOR PET ANIMALS

RELATED APPLICATIONS

The present application is a National Phase of International Application Number PCT/JP2015/064555, filed May 21, 2015, which claims priority to Japanese Application Number 2015-097238, filed May 12, 2015.

TECHNICAL FIELD

The present invention relates to an absorbent article for pet animals such as dogs and cats that is used to absorb and contain body waste of the pet animals.

BACKGROUND ART

Conventionally, absorbent articles to put on the body of a pet animal are known. For example, Patent Literature 1 discloses an absorbent article having a ventral region, a dorsal region, an intermediate region extending between the ventral and dorsal regions, a liquid-permeable interior layer sheet, a liquid-impermeable exterior layer sheet, and an absorbent core interposed between the interior and exterior layer sheets.

Patent Literature 2 discloses an absorbent article having a liquid-permeable interior layer sheet, a liquid-impermeable exterior layer sheet, and an absorbent core interposed between the interior and exterior layer sheets, wherein the absorbent article is put on a pet animal with its body encircled thereby.

PATENT LITERATURE

{PTL 1}: JP2004-159591 A
{PTL 2}: JP2012-187095 A

SUMMARY OF INVENTION

Technical Problem

An absorbent article for pet animals disclosed in PTL 1 is mainly directed to use for female dogs. The absorbent article is put on a dog by connecting the ventral and dorsal regions to each other with the dog's body inclusive of the excretion opening covered with the absorbent article so that both curved lateral edges of the absorbent article may fit along the hind legs, and whereby the absorbent article may prevent body waste from leaking out.

An absorbent article for pet animals disclosed in PTL 2 is mainly directed to use for male dogs. The absorbent article is put on the body by engaging both end portions thereof with each other with the dog's body inclusive of the excretion opening encircled with the absorbent article, and whereby the absorbent article may prevent body waste from leaking out.

However, a relatively aged pet animal (10-20 years old) is apt to be confined to a pet sheet, in other words, the so-called "bedridden" (the same hereinafter), and either the left or right side of the dog's body remains put in contact with the pet sheet in a state lying on its side. Such state over a relatively long time may cause the occurrence of pressure sores. The pressure sores may occur in a pet animal put on an absorbent article of which the inside gets stuffy under the body weight. In particular, when the aged pet animal is put on such stuffy absorbent article, which is more likely to cause the pressure sores because the inside of the absorbent article gets stuffy and wet. To prevent such matters, when a pet sheet is laid on the floor instead of the absorbent article for a pet animal, portions in places of the dog's body may undesirably be soiled, and body waste discharged by the dog may spread over the pet sheet and flow out of the pet sheet to soil the floor.

An object of the present invention is to provide an improved article suitable to bedridden pet animals.

Solution to Problem

To achieve the object, the present invention is featured in the following aspect:

An absorbent article has a longitudinal direction, a transverse direction orthogonal to the longitudinal direction, a body-facing surface, a non-body-facing surface opposed to the body-facing surface, first and second ends opposed to each other in the longitudinal direction. The article includes a tail facing area facing a dog's tail, a first section to cover one side of a dog's rump, extending from the tail facing area to the first end, a second section to cover the other side of the dog's rump, extending from the tail facing area to the second end, and an absorbent core disposed in the first and second sections.

Advantageous Effects of Invention

The absorbent article according to one or more embodiments of the present invention includes the tail facing area facing the pet animal and the first and second sections respectively covering one side and the other side of the pet animals. Thus, even when the pet animal is bedridden in a state lying on its side, the article makes it possible to quickly absorb and contain body waste discharged by the pet animal in the article without leaking out. Moreover, the article is less likely to occur stuffiness in the article due to body waste discharged by the pet animal, and thus the article makes it possible to prevent the pet animal from having pressure sores.

DESCRIPTION OF THE DRAWINGS

The drawings illustrate specific embodiments of the present invention including optional and preferred embodiments as well as essential features of the invention.

DESCRIPTION OF THE EMBODIMENTS

Figure 1:
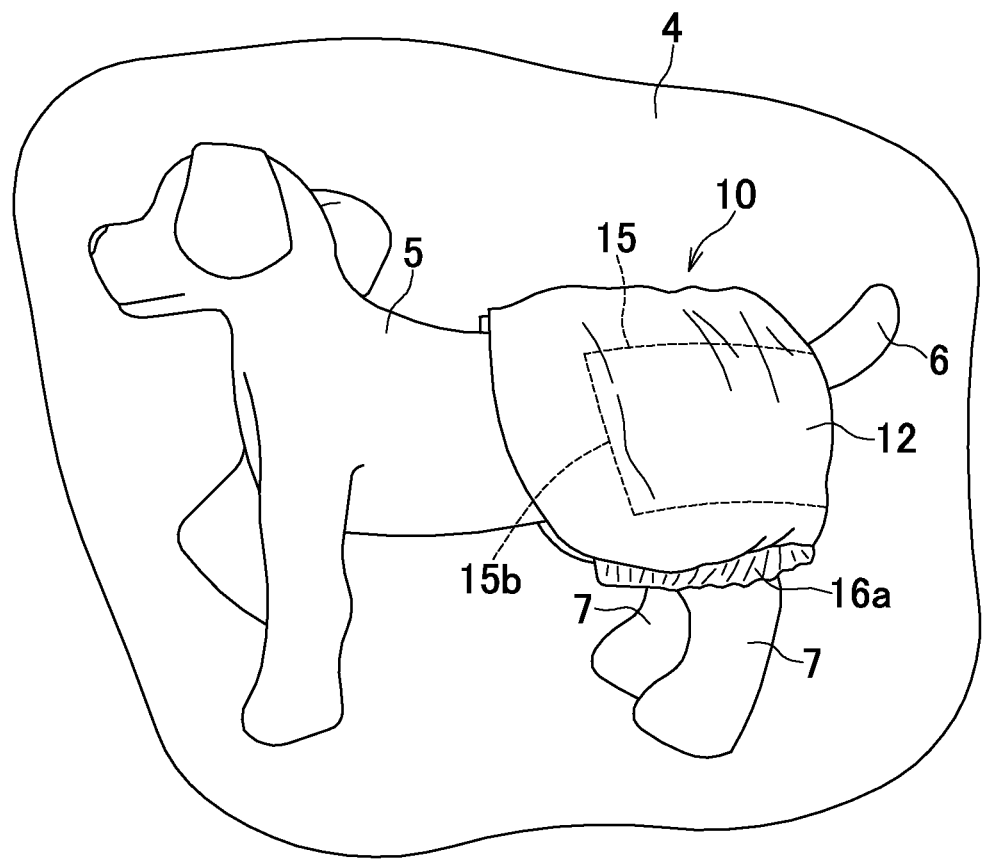
FIG. 1 is a side view from above of a dog lying on its side with the dog put on a diaper as an example of absorbent articles according to a first embodiment of the present invention.

The embodiments described below relate to a diaper as an example of absorbent articles as illustrated in FIG. 1-9, including both optional and preferred features as well as those features which are essential of the present invention. It should be noted here that a dog is simply designated as an example of pet animals in the present embodiment of the present invention.

Referring to FIGS. 1 through 4, a diaper 10 for a dog has a longitudinal direction Y, a transverse direction X being orthogonal to each other, a first axis P bisecting a dimension in the transverse direction X, a second axis Q bisecting a dimension in the longitudinal direction Y, a body-facing surface, and a non-body-facing surface opposed to the body-facing surface. The diaper 10 further has a rectangular shape contoured by a first end 10a, a second end 10b opposed to each other in the longitudinal direction Y and both side edges 10c, 10d opposed to each other in the transverse direction X.

The diaper 10 includes a tail facing area 13 facing the dog's tail 6 when a dog 5 is put on the diaper 10, a first section 11 extending from the tail facing area 13 to the first end 10a to cover one side of the dog's rump, a second section 12 extending from the tail facing area 13 to the second end 10b to cover the other side of the dog's rump, and an absorbent core 15 disposed between the first and second sections 11, 12.

The diaper 10 has, for example, a dimension L1 of about 300 mm to about 1000 mm in the longitudinal direction Y and a dimension W1 of about 80 mm to about 500 mm in the transverse direction X wherein dimensions L2, L3 of the first and second sections 11, 12 in the longitudinal direction Y respectively are about 150 mm to about 500 mm.

The diaper 10 further includes a liquid-permeable interior layer sheet 20 formed of a fibrous nonwoven fabric to define the body-facing surface, a liquid-impermeable exterior layer sheet 30 formed of a material including a moisture-permeable plastic film, a nonwoven fabric or a laminate sheet thereof to define the non-body-facing surface, and the absorbent core 15 interposed between the interior and exterior layer sheets 20, 30. A liquid-barrier sheet 40 formed of a liquid-impermeable but moisture-permeable plastic film is interposed between the absorbent core 15 and the exterior layer sheet 30. The interior and exterior layer sheets 20, 30 and liquid-barrier sheet 40 extend outboard of the peripheral edge of the absorbent core 15 and the extensions of the sheets 20, 30, 40 overlapped with one another are joined with hot melt adhesives (not shown) applied to these sheets.

A pair of elongate cover sheets 50 extending in the longitudinal direction Y are disposed on the body-facing surface of the diaper 10 along the first and second side edge 10c, 10d thereof. The cover sheets 50 are formed of a material including a nonwoven fabric or a plastic film each being liquid-permeable or liquid-impermeable, or a laminate sheet thereof. The cover sheets 50 are fixed on both lateral sides of the interior layer sheet 20 and extensions of the exterior layer sheet 30 extending outboard from both lateral sides of the interior layer sheet 20 with hot melt adhesives (not shown) to cover these lateral sides and extensions. Extension of the liquid-barrier sheet 40 extending outboard of the absorbent core 15 are overlapped with extensions of the interior layer sheet 20. In this way, the lateral sides of the interior layer sheet 20 are respectively covered with the cover sheets 20, and thus fluid body waste exuded from both lateral sides of the diaper 10 may be prevented from leaking out.

The absorbent core 15 has a rectangular shape contoured by both ends 15a, 15b opposed to each other in the longitudinal direction Y and both side edges 15c, 15d opposed to each other in the transverse direction X, and may be formed from a mixture of superabsorbent polymer (SAP) particles having a water-absorption capacity at least 10 times as high as own mass thereof, wood fluff pulp and optionally a small amount of thermoplastic fibers. The absorbent core 15 may be wrapped with a core wrapping sheet such as tissue paper (not shown) having hydrophilicity and liquid-diffusivity. The core wrapping sheet may be joined to the interior layer sheet 20 and/or the liquid-barrier 40 with hot melt adhesives (not shown).

The diaper 10 has a first side section 16, a second side section 17 each extending in the longitudinal direction Y outboard of both side edges 15c, 15d of the absorbent core 15 and an intermediate section 18 lying between the first and second side sections 16, 17. Between a side portion of the exterior layer sheet 30 defining the first side section 16 and the associated cover sheet 50, a plurality of string-like or strand-like elastic element (first elastic element) 61 extending in the longitudinal direction X are contractibly secured under tension in the longitudinal direction Y. The first side section 16 has side edge portion 16a elasticized by a contractible force of the elastic elements 61, and whereby the side edge portion 16a is formed with frill-like folds or creases.

Figure 2:
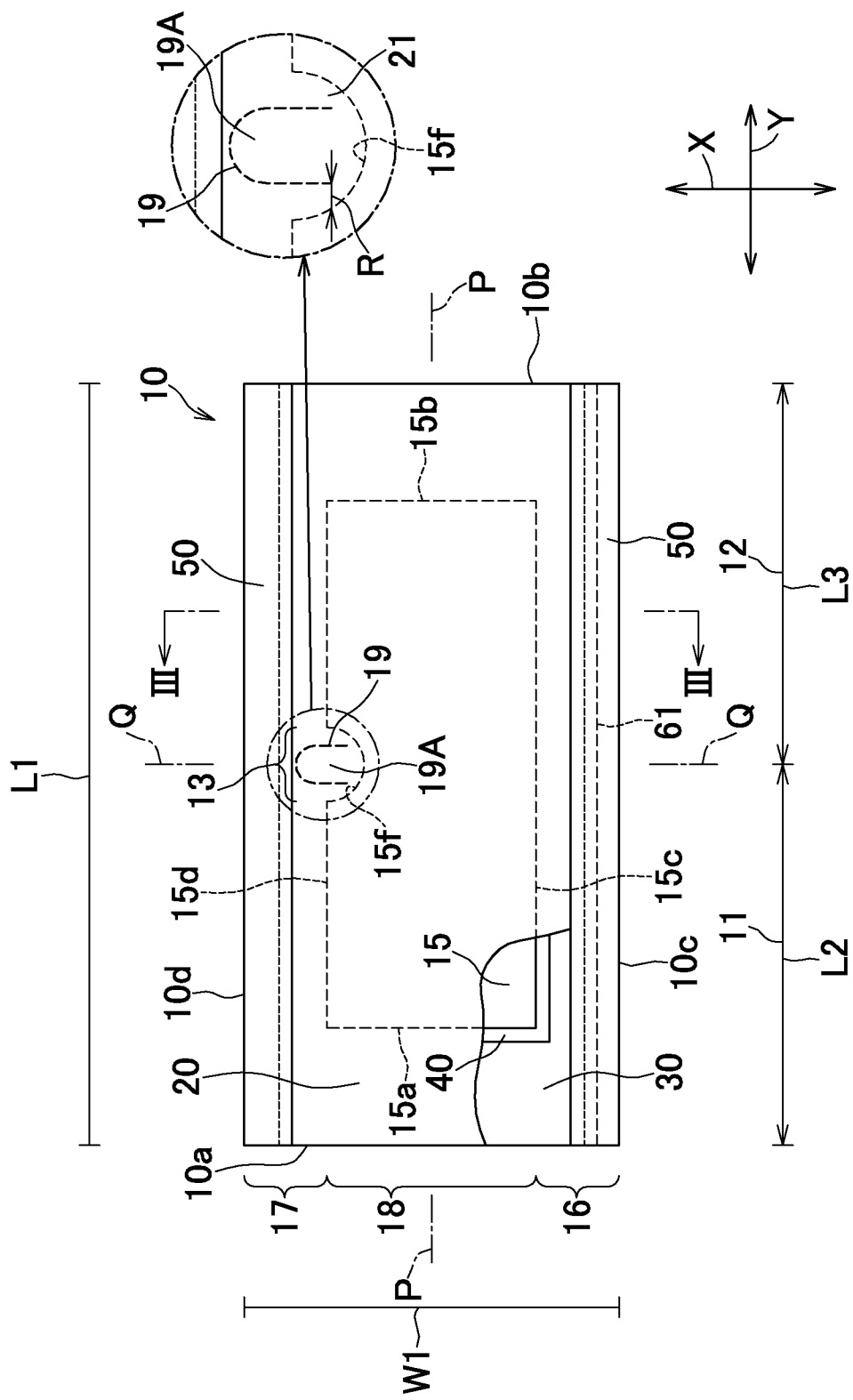
FIG. 2 is a partially cutaway and opened plan view of the diaper in which respective elastic elements are provided are stretched at the maximum in the longitudinal and transverse directions, i.e.; to the extent that gathers formed in the diaper under a contractible force of the respective elastic elements disappear.
Figure 3:
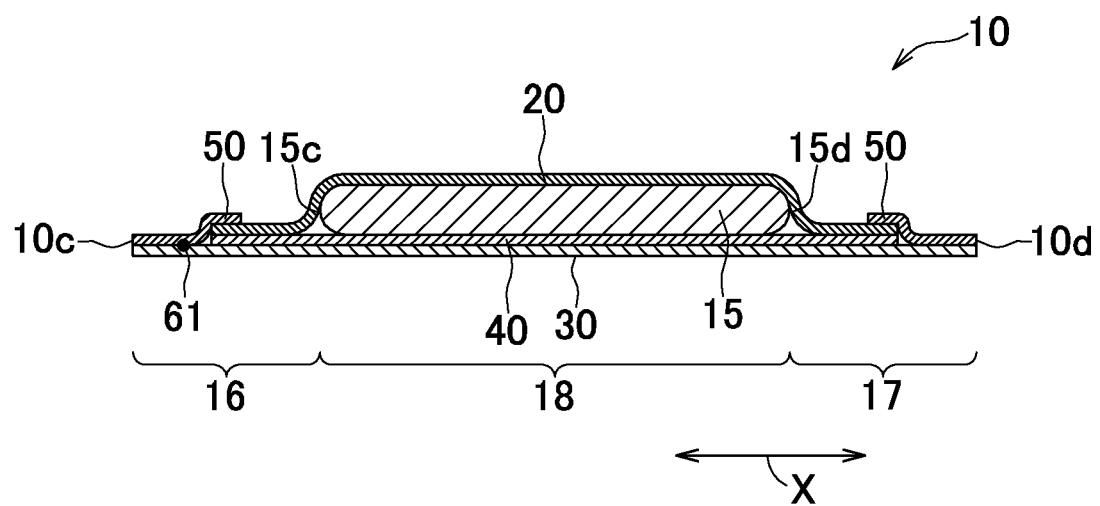
FIG. 3 is a schematic sectional view along line III-III in FIG. 2.
Figure 4:
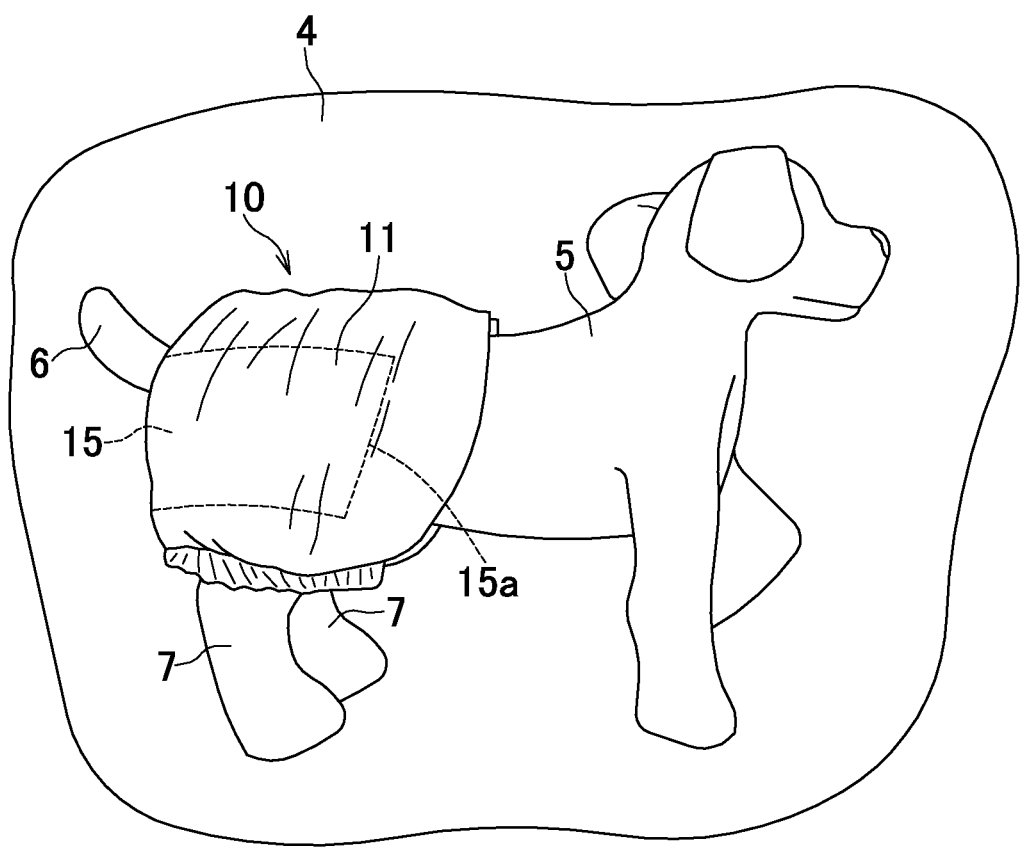
FIG. 4 is a side view from above of the dog lying on its side in a direction opposed to a lying direction of the dog in FIG. 1.

Referring to FIG. 2, the diaper 10 is provided in the tail facing area 13 with a proximately U-shaped cutting line 19 (perforations) for formation of a tail opening through which the dog's tail 6 may be passed. The cutting line 19 is passed through the interior layer sheet 20, the liquid-barrier sheet 40 and the exterior layer sheet 30 overlapped with each other in a plan view. As used herein, the term "tail facing area" refers to an area to face the dog's tail 6 when the diaper 10 is put on the dog 5, and should not be provided with the cutting line 19 such as a perforation line or a slit line. Even when a tailless dog is put on the diaper 10, the tail facing area 13 may serve as an area indicating a boundary between the first and second sections 11, 12.

The tail opening may be formed by partially cutting the diaper 10 along the cutting line 19 and folding outward a tongue-shaped portion 19A (see FIG. 5) in a joined or non-joined state of the respective sheets 20, 30. Preferably, the tail opening may have an appropriate size not only suitable for passing through the tail 6 but also for facing the dog's anus located directly below the dog's tail 6 so that body waste (feces) discharged from the dog's anus may be passed through the tail opening outward. The tongue-shaped portion 19A may be removed (cut away) from the diaper 10 to prevent body waste discharged from the dog's anus from adhering to the tongue-shaped portion 19A.

The tail facing area 13 having the cutting line 19 is located in a concave portion 15f curved inward in the transverse direction X in an approximately mid portion of the side edge 15d of the absorbent core 15, with part of the tail facing area 13 overlapped with the absorbent core 15 in the longitudinal direction Y. Since the tail facing area 13 is located in the concave portion 15f, the absorbent core 15 and the cutting line 19 are spaced apart from each other by a given dimension and a non-positional area 21 of the absorbent core 15 is formed between the absorbent core 15 and the cutting line 19. When the absorbent core 15 and the cutting line 19 are overlapped with each other or they are close to each other, fluid body waste absorbed and spread by the absorbent core 15 may leak out from the tail opening formed by cutting along the cutting line 19; however, such a given spaced-apart dimension makes it possible to prevent such a leakage. Moreover, such a given spaced-apart dimension makes it possible to prevent the occurrence of creases and deformation of the absorbent core 15 such as lowering the absorption performance of the absorbent core 15 under the movement of the dog's tail 6 applied directly to the absorbent core 15. To achieve such effects, a spaced-apart dimension R between the absorbent core 15 and the cutting line 19 is preferably at least 5 mm or more and not more than 100 mm. It should be noted here that though the cutting line 19 in the present embodiment is provided only in the side of the second side edge 17, the cutting line 19 may be provided in both sides of the first and second sections 16, 17, respectively.

Though the tail facing area 13 is provided with the cutting line 19 formed by perforations, rather than the perforations, the tail facing area 13 may have an tail opening suitable to pass through the dog's tail 6 formed by partially cutting out the absorbent core 10. The tail facing area 13 may also be formed with a notch convexly extending from the second side edge 10b toward the first axis P as long as the notch is suitable to pass through the dog's tail 6. Though the cutting line 19 has a shape such as convexly curving outside in the transverse direction X, the cutting line 19 may have a line-like, round-like or rectangular-like shape according to a size and shape of the dog's tail 6.

The cutting line 19 in the present embodiment is formed so as to cross the second axis Q and to be symmetrical with respect thereto. As previously described, the first and second sections 11, 12 respectively extend from the tail facing area 13 having the cutting line 19 to the first and second ends 10a, 10b, more specifically, from the second axis Q to the first and second ends 10a, 10b. Thus, a dimension L2 in the longitudinal direction Y of the first section 11 and a dimension L3 in the longitudinal direction Y of the second section 12 are approximately equal to each other and the dimensions L2, L3 respectively account for about 50% of a dimension L1 in the longitudinal direction Y of the diaper 10. Even when either the left or right side of the dog 5 is put in contact with the floor 4, preferably, the dimension L2 of the first section 11 and the dimension L3 of the second section 12 are approximately equal to each other so that the absorption capacity of fluid body waste in the first section 11 may be approximately equal to that in the second section 12. However, when one of the left and right sides of the dog 5 is put in contact with the floor 4, fluid body waste discharged in the diaper 10 is likely to more flow to the one of the left and right sides of the dog 5 put in contact with the floor 4 (downward side) than the other of the dog 5. Accordingly, for example, one of the dimensions L2, L3 may be greater than the other. Here the cutting line 19 may be biased to the first end 10a side or the second end 10b side without crossing the second axis Q, and the first and second sections 11, 12 may be divided with reference to a center in the longitudinal direction Y of the tail facing area 13 (or the cutting line 19). Consequently, for example, the dimensions L2, L3 may be in relationship with one of them being greater than the other of them and vice versa, example, the dimension L2 may be 40%-60% of the dimension L1 and the dimension L3 may be 60%-40% of the dimension L1.

Figure 5:
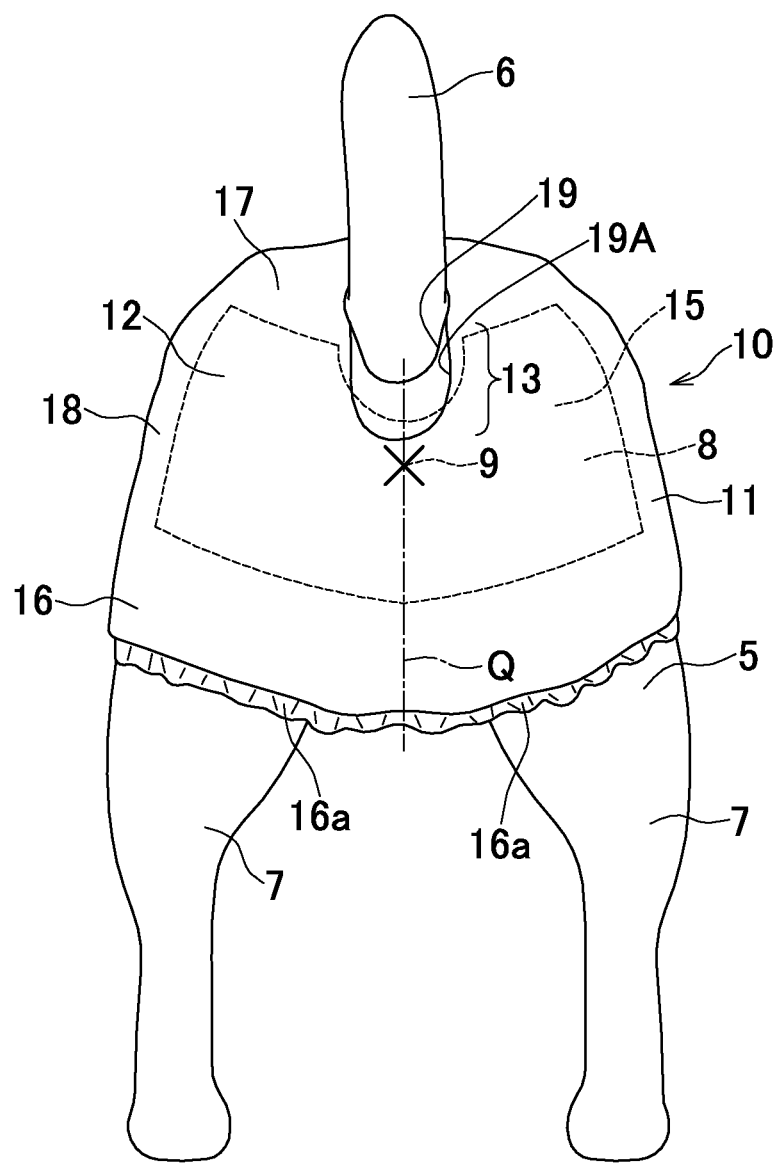
FIG. 5 is a rear view from behind of the dog in FIG. 1 in its standing state.

Referring to FIG. 5, when the dog 5 is put on the diaper 10, the diaper 10 is partially cut out along the cutting line 19 to form a tail opening, and the dog's tail 6 is passed through the tail opening with the body-facing surface of the diaper 10 put in contact with the dog's rump. By passing the tail 6 through the tail opening, the diaper 10 should unintendedly not be removed from the dog's body even when the dog 5 is in a standing or side lying posture. For the dog being a female, the female dog's anus 9 is located in the positional area of the absorbent core 15 and fluid body waste discharged by the dog may be quickly absorbed and contained by the absorbent core 15.

Referring again to FIG. 1, a relatively aged dog 5 (more than 10 years old) may not maintain lying on its belly even when the dog takes a rest of its body, and may be bedridden with the dog 5 put in contact with a pet sheet on the floor 4. When the dog 5 discharges in such a lying state, the discharged fluid body waste may flow to the dorsal and/or rump side of the dog 5 on the floor 4. A conventional diaper for female dogs of a type to connect the ventral and dorsal regions of the diaper 10 and a conventional diaper for male dogs of a type to connect both ends of the diaper 10 encircling the dog's body are respectively designed on the assumption that the dog 5 discharges fluid body waste in a standing posture, a sitting posture or a posture of lying on its face. Here such diapers are put on the dog 5 to cover the dog's rump with an positional area of the absorbent core 15 formed long in the longitudinal direction Y positioned on the dog's body along the front-back direction thereof. Thus, when the dog 5 lies on its side, an area of the absorbent core 15 put in contact with the floor 4 is relatively small, and in consequence, the discharged fluid body waste spreads to the dorsal and rump sides of the dog 5 in the diaper 10 should not be sufficiently absorbed and contained by the absorbent core 15 and may leak out of the diaper 10. This kind of diaper for dogs has its inside spaces closed to prevent fluid body waste from leaking out. Consequently, the inside of the diaper 10 may easily get stuffy, and when the dog 5 lies on its side over a relative long time under the body weight, pressure sores may occur and deteriorate. To prevent the pressure sores due to such stuffiness in the diaper 10 from occurring, when the dog 10 is laid on a pet sheet on the floor 4, the dog's body may be soiled by fluid body waste spread over a relatively wide range of the pet sheet.

According to the diaper 10 of the present embodiment, the absorbent core 15 having a relatively wide area is located in the first and second sections 11, 12, and thus, when the dog 5 put on the diaper 10 lies on its side on the floor 4, one of the left and right side of the dog's body put in contact with the floor 4 is entirely covered by the one of the first and second sections 11, 12 put in contact with the floor 4, and a relative large amount of fluid body waste discharged from the dog's excretion opening in the diaper 15 may be quickly absorbed by the absorbent core 15 and the fluid body waste may be prevented from leaking out of the diaper 10. Moreover, though the diaper 10 is not provided with fastening means for securing the diaper 10 on the dog's body, the diaper 10 may be prevented from causing the positional displacement with respect to the dog's body by only passing the dog's tail 6 through the tail opening during wearing the diaper 10. Thus, the inside of the diaper 10 may be in an open state without being completely closed up, so that the occurrence and deterioration of pressure sores may be inhibited.

Furthermore, to prevent the occurrence of pressure sores, a caregiver needs t0 turn a direction (up-and-down direction) that a dog lies on its side. For example, as shown in FIG. 1, after the required time has elapsed from the time when the dog 5 was lying on the floor 4 (for example, after 2 hours has elapsed), the caregiver needs to turn the dog's lying direction, from a state lying on its side with the first section 11 of the diaper 10 put in contact with the floor 4, to a state lying on its side with the second section 12 of the diaper 10 put in contact with the floor 4.

Optionally, the diaper 10 may be provided with fastening means to connect the first and second sections 11, 12; however, even when not provided, as previously described, since the dog's tail 6 is passed through the tail opening formed by the cutting line 19, the diaper 10 should not be removed from the dog 5 put thereon. Moreover, the caregiver's handling to turn the dog's side lying posture of the dog put on the diaper 10 may quickly be performed by putting, for example, the first side edge 16 of the diaper 10 in contact with the rear leg of the dog 5 under a contractible force of the elastic elements 61 provided in the diaper 10 without other handling. Furthermore, even when the caregiver moves the dog lying on its side on the floor 4, the first side edge 16 should not be separated of the rear leg 7 of the dog 5 and curled or folded.

According to a conventional diaper for pet animals such as dogs, which are usually used in this kind of technical field, the diaper are put on the dog 5 with the longitudinal direction of the diaper aligned with that of the dog's body. However, according to the present embodiment, the diaper 10 is put on the dog 5 with the longitudinal direction Y of the diaper 10 crossed with the longitudinal direction of the dog 5 so that the absorbent core 15 may extend in the cross direction, whereby the leakage of fluid body waste discharged by the dog 5 and the occurrence of pressure sores are effectively prevented.

Second Embodiment

The basic structure of the diaper 10 according to a second embodiment of the present invention is substantially the same as that of the first embodiment of the present invention. Accordingly, for the second embodiment, only the basic structure different from that of the first embodiment is hereinafter described.

Referring to FIG. 6 through FIG. 9, the diaper 10 is provided with a second elastic element 62 extending in the longitudinal direction Y in the second edge section 17, and whereby the second edge section 17 is formed with a frill-like elastic edge under a contractible force of the second elastic element 62.

The diaper 10 further is provided with a pair of upstanding cuff flaps 70 extending in the longitudinal direction along the first and second side edges 10c, 10d, respectively. The upstanding cuff flaps 70 respectively have end portions fixed on the interior layer sheet 20 adjacent to the first and second ends 10a, 10b; proximal edge portions 73 fixed on the interior layer sheet 20, extending in the longitudinal direction Y between the first and second ends 10a, 10b; and distal edge portions 74 respectively positioned inboard of the proximal edge portions 73. The distal edge portions 74 respectively have sleeve-like edges 74a within which third elastic elements (cuff elastics) 63 are contractibly secured under tension in the longitudinal direction Y. The distal edge portions 74 are spaceable away from the interior layer sheet 20 toward the dog's body to form upstanding cuffs (barrier cuffs) when the diaper 10 is put on the dog 5. This makes it possible to prevent fluid body waste discharged in the diaper 10 from flowing to the dorsal side and hind legs of the dog 5.

Figure 8:
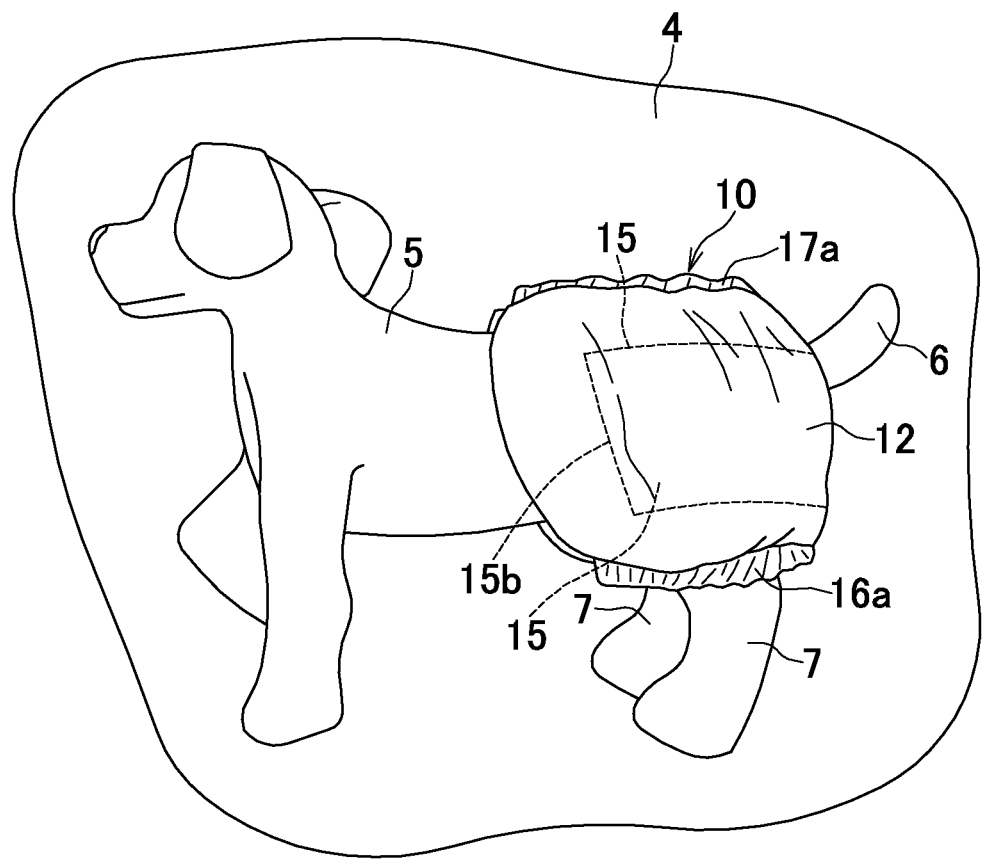
FIG. 8 is a side view from above of the dog lying on its side with the dog put on the diaper according to the second embodiment of the present invention.
Figure 9:
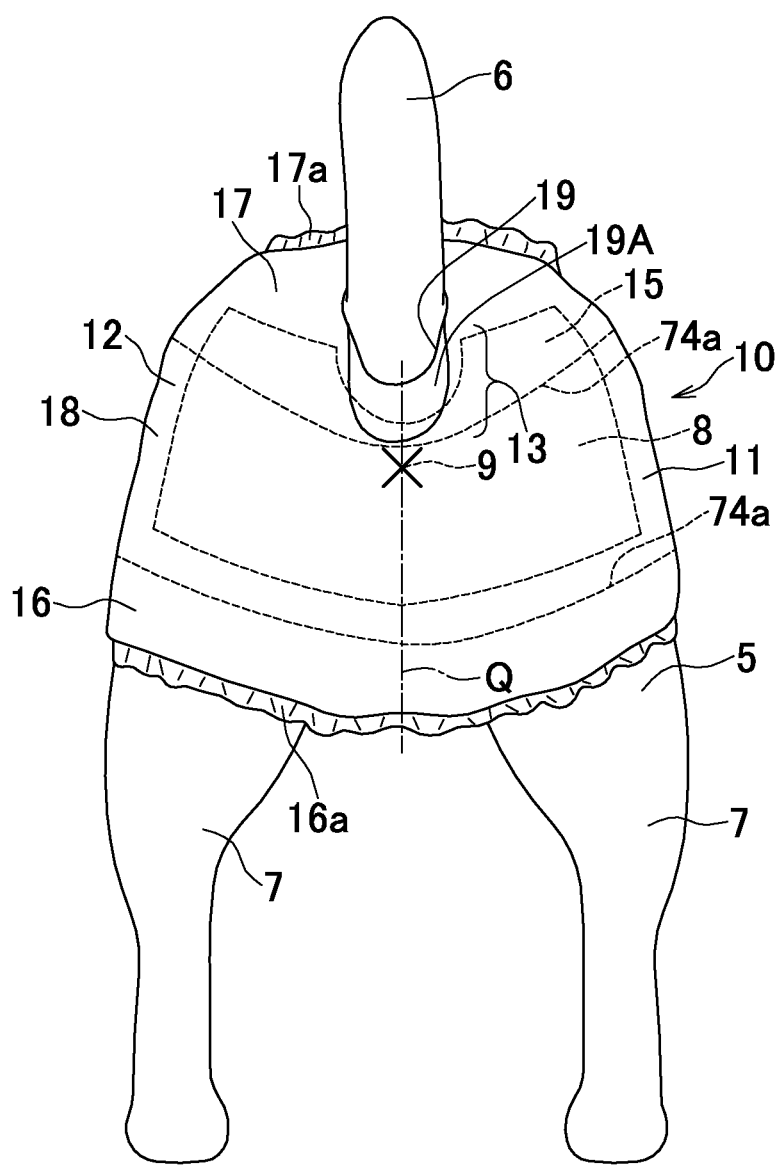
FIG. 9 is a rear view from behind of the dog put on the diaper in its standing state according to the second embodiment of the present invention.

The first and second elastic elements 61, 62 located in the first and second edge sections 16, 17 respectively are contractibly secured under tension between the proximal edge portions 73 of the upstanding cuff flap 70 and portions of the exterior layer sheet 30 extending outboard beyond outer side edges of the interior layer sheet 20. Referring to FIGS. 8 and 9, the side edge 16a of the first side section 16 is elasticized under a contractible force of the first elastic element 61 so that the elasticized edge 16a may be fitted to the hind legs 7 of the dog 5, while the side edge 17a of the second side section 17 is elasticized under a contractible force of the second elastic element 62 so that the elasticized edge 17a may be fitted to the dorsal side of the dog 5. In this way, since the side edge 17a of the second side section 17 as well as the side edge 16a of the first side section 16 may be fitted to the dog's body, the positional displacement of the diaper 10 with respect to the dog's body may more effectively prevented in the second embodiment than in the first embodiment. Moreover, fluid body waste flowed to the dorsal side of the dog's body beyond the upstanding cuff flaps 70 may be prevented from leaking out.

Figure 6:
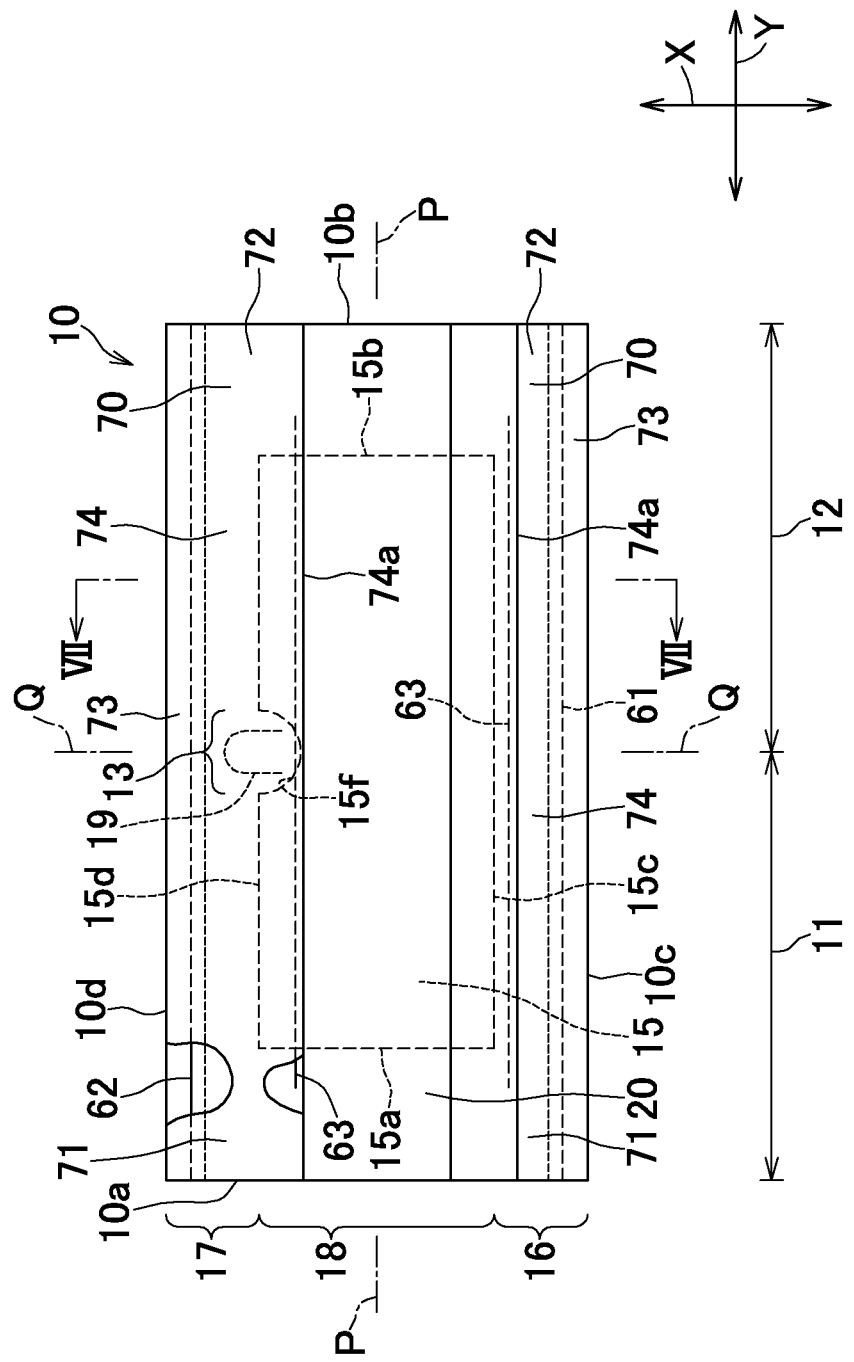
FIG. 6 is a partially cutaway and opened view similar to FIG. 2 according to a second embodiment of the present invention.
Figure 7:
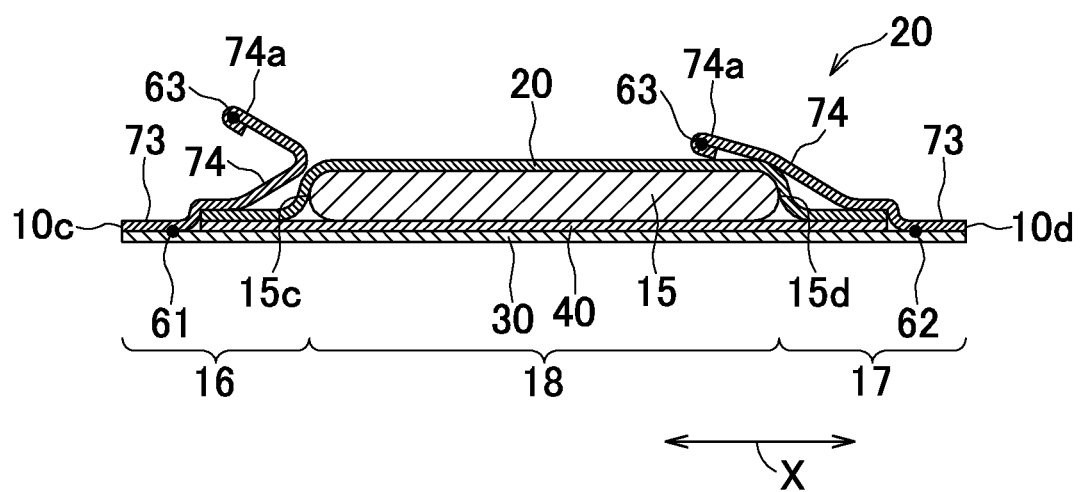
FIG. 7 is a schematic sectional view along line VII-VII in FIG. 6.

Referring to FIGS. 6 and 7, the upstanding cuff flap 70 disposed in the first side section 16 is fixed to the body-facing surface of the interior layer sheet 20 with a portion of the upstanding cuff flap 70 collapsed outward in the transverse direction X between the end portions 71, 72 thereof. When the diaper 10 is put on the diaper 10, the collapsed portion of the upstanding cuff flap 70 faces the hind legs 7 of the dog 5 and the edge 74a of the distal edge portion 74 elasticized by the cuff elastic element 63 is put in contact with the dog's legs 7 together with the side edge of the diaper 10 elasticized by the first elastic element 61 inclusive of the proximal edge 73 of the upstanding cuff flap 70. This makes it possible to prevent the occurrence of the positional displacement of the diaper 10 with respect to the dog's body from occurring.

On the other hand, the upstanding cuff flap 70 disposed in the second side section 17 is fixed to the body-facing surface of the interior layer sheet 20 with the edge 74a elasticized by the cuff elastic elements 63 of the distal edge portion 74 located inboard of the proximal edge portion 73, in other words, with the upstanding cuff flap 70 collapsed inward in the transverse direction X. In this way, the cutting line 19 of the diaper 10 is covered with the distal edge portion 74 and the dog's tail 6 is put and covered in contact with the distal edge portion 74 inclusive of the edge 74a elasticized by the cuff elastic element 63. This makes it possible to prevent the dog's tail 6 from being removed out of the tail opening. Thus, the upstanding cuff flaps 70 may function not only as barriers against the leakage of body waste but also as enhancing the fitness to the dog's body. Referring to FIG. 9, when the dog 5 put on the diaper 10 is a female, the distal edge portion 74 inclusive of the edge 74a of the upstanding cuff flap 70 disposed in the second side section 17, which is spaced away from the interior layer sheet 20 toward the female dog 5, is put in contact with the vicinity of the excretion opening thereof. This makes it possible to effectively prevent fluid body waste discharged in the diaper 10 from flowing, from the middle portion 18 in which the absorbent core 15 is positioned, to the side sections 16, 17 of the diaper 10.

Unlike the present embodiment, the standing cuff flap 70 in the first section 16 may be collapsed inward in the transverse direction X and the standing cuff flap 70 in the second side section 17 may be collapsed outward in the transverse direction X, and the end portions 71, 72 of the standing cuff flaps 70 may not be fixed to the interior layer sheet 20. When the end portions 71, 72 are not fixed to the interior layer sheet 20, the standing cuff flaps 70 may be collapsed inward and/or outward in the transverse direction X over a full length thereof, if necessary.

Referring again to FIG. 6, the cutting line 19 in the tail facing area 13 is provided between the second elastic elements 62 located outside in the transverse direction X and the third elastic element 63 located inside in the transverse direction X. In this way, the cutting line 19 is interposed between these elastic elements 62, 63 and in such interposed state, a portion adjacent to the tail opening formed by cutting out the cutting line 19 is put in contact with the dog's body, and thus, it is possible to prevent fluid body waste from leaking out of the tail opening.

To achieve such effects, the second elastic element 62 is preferably located adjacently to one end of the tail opening in the second section 17, the third elastic element 63 is preferably located adjacently to the other end of the tail opening.

The constituent elements of the diaper 10 are not limited to those described in the present specification but other various types of materials widely used in the relevant technical filed may be used without limitation unless otherwise stated. As used herein, the term such as "first", "second" and "third" of the present specification and claims are used merely to distinguish the similar elements, similar positions or other similar means.

The present disclosure relating to the present invention described above may be arranged by at least the following features:

The diaper has a longitudinal direction, a transverse direction orthogonal to the longitudinal direction, a body-facing surface, a non-body-facing surface opposed to the body-facing surface, first and second ends opposed to each other in the longitudinal direction, and includes a tail facing area facing a dog's tail, a first section to cover one side of a dog's rump, extending from the tail facing area to the first end, a second section to cover the other side of the dog's rump, extending from the tail facing area to the second end, and an absorbent core disposed in the first and second sections.

The diaper according to present invention disclosed above [0040] may include at least the following embodiments, which may be taken in isolation from or in combination with one another.

(1) The diaper has both side sections in the transverse direction, one of both side sections is provided with the tail facing area, the other of both side section is provided with a first elastic elements.

(2) The diaper is provided with a second elastic elements in the one of both side sections.

(3) The diaper includes a liquid-permeable interior layer sheet covering a side of the body-facing surface of the absorbent core, and a liquid-impermeable exterior layer sheet covering a side of the non-body-facing surface of the absorbent core.

(4) The first and second elastic elements are secured between a sheet located to a side of the body-facing surface and the exterior layer sheet.

(5) The sheet located to the body-facing surface is liquid-impermeable.

(6) The diaper includes a standing cuff flap disposed in at least one of both side sections, the standing cuff flap has both end portions fixed to the interior layer sheet in the first and second ends, a proximal edge portion fixed to the interior layer sheet, extending in the longitudinal direction between both the end portions, and a distal edge portion provided with a cuff elastic element.

(7) The standing cuff flap is collapsed inward in the transverse direction.

(8) The standing cuff flap is collapsed outward in the transverse direction in both ends thereof.

(9) Part of the tail facing is overlapped with the absorbent core in the longitudinal direction, and a non-positional area is positioned around a cutting line for forming a tail opening in the tail facing area.

(10) The tail facing area has one of a tail opening and a cutting line of perforations for forming a tail opening.

REFERENCE SIGNS LIST 5 pet animal (dog)
6 dog's tail
10 absorbent article (diaper) for pet animal
11 first section
12 second section
13 tail facing area
15 absorbent core
20 interior layer sheet
21 non-positional area of absorbent core
30 exterior layer sheet
61 first elastic element
62 second elastic element
63 third elastic element
70 standing cuff flap
71, 72 end portions of standing cuff flap
73 proximal edge portion
74a distal edge portion having edge
X transverse direction
Y longitudinal direction

The invention claimed is:

1. An absorbent article for a pet animal having a longitudinal direction, and a transverse direction orthogonal to the longitudinal direction, said absorbent article comprising:
a body-facing surface and a non-body-facing surface opposed to the body-facing surface;
first and second ends opposed to each other in the longitudinal direction,
a tail facing area configured to face a dog's tail;
a first section configured to cover one side of a dog's rump and extending from the tail facing area to the first end;
a second section configured to cover the other side of the dog's rump and extending from the tail facing area to the second end; and
an absorbent core disposed in the first and second sections,
wherein
the absorbent core includes side edges opposed to each other in the transverse direction,
one of the side edges includes a concave portion curved inward in the transverse direction,
the tail facing area is located in the concave portion, and
the tail facing area includes a tail opening or a cutting line of perforations for forming a tail opening.

2. The absorbent article according to claim 1, further comprising two side sections opposed to each other in the transverse direction, wherein one of the side sections is provided with the tail facing area, and the other of the side sections is provided with a first elastic element.

3. The absorbent article according to claim 2, wherein said one of the side sections is provided with a second elastic element.

4. The absorbent article according to claim 3, further comprising:
   a liquid-permeable interior layer sheet covering the absorbent core on a side facing the body-facing surface, and
   a liquid-impermeable exterior layer sheet covering the absorbent core on a side facing the non-body-facing surface.

5. The absorbent article according to claim 4, further comprising a sheet on a side of the body-facing surface, wherein the first and second elastic elements are secured between the sheet and the exterior layer sheet.

6. The absorbent article according to claim 5, wherein the sheet is liquid-impermeable.

7. The absorbent article according to claim 4, further comprising a standing cuff flap disposed in at least one of the side sections, wherein
   the standing cuff flap has
      two end portions fixed to the interior layer sheet in the first and second ends,
      a proximal edge portion fixed to the interior layer sheet and extending in the longitudinal direction between the end portions, and
      a distal edge portion provided with a cuff elastic element.

8. The absorbent article according to claim 7, wherein the standing cuff flap is collapsed inward in the transverse direction.

9. The absorbent article according to claim 7, wherein the standing cuff flap is collapsed outward in the transverse direction.

10. The absorbent article according to claim 1, wherein
   the tail facing area includes the cutting line defining the tail opening, and
   the cutting line is spaced away from the concave portion by a non-positional area of the absorbent core.

* * * * *